United States Patent
Brew et al.

(10) Patent No.: US 8,030,357 B2
(45) Date of Patent: Oct. 4, 2011

(54) USE OF BUPROPION METABOLITES FOR THE TREATMENT OF INFLAMMATORY DISORDERS

(75) Inventors: John Brew, Saffron Walden (GB); Robin Mark Bannister, Saffron Walden (GB); Andrew Douglas Baxter, Cambridge (GB)

(73) Assignee: Biocopea Limited, London (GB)

( * ) Notice: Subject to any disclaimer, the term of this patent is extended or adjusted under 35 U.S.C. 154(b) by 314 days.

(21) Appl. No.: 12/282,274

(22) PCT Filed: Mar. 9, 2007

(86) PCT No.: PCT/GB2007/000868
§ 371 (c)(1), (2), (4) Date: Mar. 10, 2009

(87) PCT Pub. No.: WO2007/102019
PCT Pub. Date: Sep. 13, 2007

(65) Prior Publication Data
US 2009/0318562 A1 Dec. 24, 2009

(30) Foreign Application Priority Data
Mar. 9, 2006 (GB) .................................. 0604824.3

(51) Int. Cl.
*A61K 31/138* (2006.01)
(52) U.S. Cl. ........................................................ 514/653
(58) Field of Classification Search .................... 514/653
See application file for complete search history.

(56) References Cited

U.S. PATENT DOCUMENTS
2002/0052341 A1  5/2002  Fang et al.

FOREIGN PATENT DOCUMENTS
WO  WO 01/62257 A  8/2001

OTHER PUBLICATIONS

Brustolim et al. "A new chapter opens in anti-inflammatory treatments: The antidepressant Bupropion lowers production of tumor necrosis factor and interferon-gamma in mice" *International Immunopharmacology*, 2006, pp. 903-907, vol. 6.
Modell et al. "Treatment of atopic dermatitis and psoriasis vulgaris with bupropion-SR: A pilot study" *Psychosomatic Medicine*, 2002, pp. 835-840, vol. 64.
Bondarev, M. L. et al, "Behavioral and biochemical investigations of bupropion metabolites," *European Journal of Pharmacology*, pp. 85-93, vol. 474, No. 1, Amsterdam, NL.
Kast R.E., "Evidence of a mechanism by which etanercept increased TNF-alpha in multiple myeloma: New insights into the biology of TNF-alpha giving new treatment opportunities—the role of bupropion," *Leukemia Research*, Dec. 2005, pp. 1459-1463, vol. 29, No. 12, New York, NY, US.
Musso, D. L. et al, "Synthesis and evaluation of the anticonvulsant activity of a series of 2-amino-1-phenyl-1-propanols derived from the metabolites of the antidepressant bupropion," *Bioorganic & Medicinal Chemistry Letters*, Jan. 7, 1997, pp. 1-6, vol. 7, No. 1, Oxford, GB.

*Primary Examiner* — Jennifer M Kim
(74) *Attorney, Agent, or Firm* — Saliwanchik, Lloyd & Eisenschenk

(57) ABSTRACT

Compounds that may be used for the treatment or prevention of a condition associated with T-cell proliferation or that is mediated by pro-inflammatory cytokines are of formula (I)

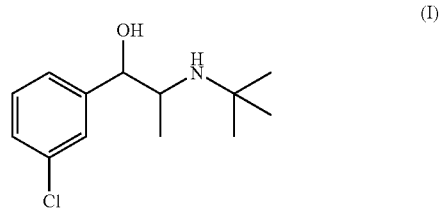

or a salt thereof.

5 Claims, No Drawings

USE OF BUPROPION METABOLITES FOR THE TREATMENT OF INFLAMMATORY DISORDERS

This application is a National Stage Application of International Application Number PCT/GB2007/000868, filed Mar. 9, 2007; which claims priority to Great Britain Patent Application No. 0604824.3, filed Mar. 9, 2006, all of which are incorporated herein in their entirety.

FIELD OF THE INVENTION

This invention relates to the use of buproprion metabolites for the treatment of inflammatory disorders.

BACKGROUND OF THE INVENTION

Immune-driven inflammatory events are a significant cause of many chronic inflammatory diseases where prolonged inflammation causes tissue destruction and results in extensive damage and eventual failure of the effected organ. The cause of these diseases is unknown, so they are often called autoimmune, as they appear to originate from an individual's immune system turning on itself. Conditions include those involving multiple organs, such as systemic lupus erythematosus (SLE) and scleroderma. Other types of autoimmune disease can involve specific tissues or organs such as the musculoskeletal tissue (rheumatoid arthritis, ankylosing spondylitis), gastro-intestinal tract (Crohn's disease and ulcerative colitis), the central nervous system (Alzheimer's, multiple sclerosis, motor neurone disease, Parkinson's disease and chronic fatigue syndrome), pancreatic beta cells (insulin-dependent diabetes mellitus), the adrenal gland (Addison's disease), the kidney (Goodpasture's syndrome, IgA nephropathy, interstitial nephritis), exocrine glands (Sjogren's syndrome and autoimmune pancreatitis) and skin (psoriasis and atopic dermatitis).

In addition, there are chronic inflammatory diseases whose aetiology is more or less known but whose inflammation is also chronic and unremitting. These also exhibit massive tissue/organ destruction and include conditions such as osteoarthritis, periodontal disease, diabetic nephropathy, chronic obstructive pulmonary disease, artherosclerosis, graft versus host disease, chronic pelvic inflammatory disease, endometriosis, chronic hepatitis and tuberculosis. In these diseases, the tissue destruction often damages organ function, resulting in progressive reductions in quality of life and organ failure. These conditions are a major cause of illness in the developing world and are poorly treated by current therapies.

Inflammation of skin structures (dermatitis) is a common set of conditions which include actinic keratosis, acne rosacea, acne vulgaris, allergic contact dermatitis, angioedema, atopic dermatitis, bullous pemiphigoid, cutaneous drug reactions, erythema multiforme, lupus erythrametosus, photodermatitis, psoriasis, psoriatic arthritis, scleroderma and urticaria. These diseases are treated using a wide array of therapies, many of which have very severe side-effects.

Current disease-modifying treatments (if any) for immune-driven conditions include neutralising antibodies, cytotoxics, corticosteroids, immunosuppressants, antihistamines and antimuscarinics. These treatments are often associated with inconvenient routes of administration and severe side-effects, leading to compliance issues. Moreover, certain drug classes are only effective for certain types of inflammatory diseases, e.g. antihistamines for rhinitis.

Bupropion is a marketed anti-depressant with serotonin and noradrenaline reuptake inhibition as its central mechanism of action. Metabolites of bupropion are described in the literature as having therapeutic utility in various diseases of the central nervous system.

SUMMARY OF THE INVENTION

Surprisingly, it has been found that selected bupropion metabolites are modulators of cytokines and possess anti-inflammatory properties. According to the present invention an inflammatory condition, e.g. described above, is treated by the use of a compound of general formula (I)

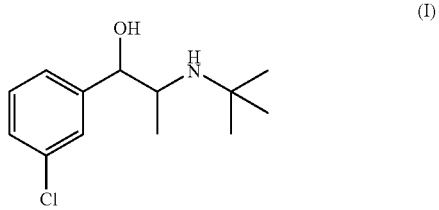

or a salt thereof.

DESCRIPTION OF THE INVENTION

While bupropion itself has very weak cytokine modulatory activity in the LPS-induced model of cytokine release, compounds of formula (I) are surprisingly potent cytokine modulators. Bupropion is metabolised non-stereoselectively to all four enantiomers of formula (I), but these compounds represent a relatively small proportion of the total metabolism of the parent drug.

Compounds for use in the invention are chiral, and it will be understood that this invention includes any diastereomers and enantiomers of (I). A preferred diastereomer or enantiomer of (I) has little or no monoamine reuptake activity but displays potent cytokine modulatory activity. These activities may be determined by use of the appropriate in vitro and in vivo assays. Particularly preferred compounds include the erythro-pair of diastereoisomers and the individual erythro enantiomers. These particularly preferred compounds are (1S,2R)-erythro-2-(1,1-dimethylethyl)amino-1-(3-chlorophenyl)propan-1-ol and (1R,2S)-erythro-2-(1,1-dimethylethyl)amino-1-(3-chlorophenyl)propan-1-ol. It is understood that compounds for use in the invention include pharmaceutically active salts, e.g. the hydrochloride.

The compounds of formula (I) according to the invention are used to treat inflammatory diseases including, but not exclusive to, autoimmune diseases involving multiple organs, such as systemic lupus erythematosus (SLE) and scleroderma, specific tissues or organs such as the musculoskeletal tissue (rheumatoid arthritis, ankylosing spondylitis), gastrointestinal tract (Crohn's disease and ulcerative colitis), the central nervous system (Alzheimer's, multiple sclerosis, motor neurone disease, Parkinson's disease and chronic fatigue syndrome), pancreatic beta cells (insulin-dependent diabetes mellitus), the adrenal gland (Addison's disease), the kidney (Goodpasture's syndrome, IgA nephropathy, interstitial nephritis) exocrine glands (Sjogren's syndrome and autoimmune pancreatitis) and skin (psoriasis and atopic dermatitis), chronic inflammatory diseases such as osteoarthritis, periodontal disease, diabetic nephropathy, chronic obstructive pulmonary disease, artherosclerosis, graft versus host disease, chronic pelvic inflammatory disease, endometriosis, chronic hepatitis and tuberculosis, IgE mediated (Type I) hypersensitivities such as rhinitis, asthma, anaphylaxis and dermatitis. Dermatitis conditions include actinic keratosis, acne rosacea, acne vulgaris, allergic contact dermatitis, angioedema, atopic dermatitis, bullous pemiphigoid, cutaneous drug reactions, erythema multiforme, lupus erythrametosus, photodermatitis, psoriasis, psoriatic arthritis, scleroderma and urticaria. Conditions of the eye, such as diabetic retinopathy, macular degeneration, choroidal neovascular membrane, cystoid macular edema, epi-retinal membrane, macular hole, dry eye, uveitis and conjunctivitis, may also be treated.

These compounds may be used according to the invention when the patient is also administered or in combination with another therapeutic agent selected from corticosteroids (examples including cortisol, cortisone, hydrocortisone, dihydrocortisone, fludrocortisone, prednisone, prednisolone, deflazacort, flunisolide, beconase, methylprednisolone, triamcinolone, betamethasone, and dexamethasone), disease modifying anti-rheumatic drugs (DMARDs) (examples including azulfidine, aurothiomalate, bucillamine, chlorambucil, cyclophosphamide, leflunomide, methotrexate, mizoribine, penicillamine and sulphasalazine), immunosuppressants (examples including azathioprine, cyclosporin, mycophenolate), COX inhibitors (examples including aceclofenac, acemetacin, alcofenac, alminoprofen, aloxipirin, amfenac, aminophenazone, antraphenine, aspirin, azapropazone, benorilate, benoxaprofen, benzydamine, butibufen, celecoxib, chlorthenoxacine, choline salicylate, chlometacin, dexketoprofen, diclofenac, diflunisal, emorfazone, epirizole, etodolac, feclobuzone, felbinac, fenbufen, fenclofenac, flurbiprofen, glafenine, hydroxylethyl salicylate, ibuprofen, indometacin, indoprofen, ketoprofen, ketorolac, lactyl phenetidin, loxoprofen, mefenamic acid, metamizole, mofebutazone, mofezolac, nabumetone, naproxen, nifenazone, oxametacin, phenacetin, pipebuzone, pranoprofen, propyphenazone, proquazone, rofecoxib, salicylamide, salsalate, sulindac, suprofen, tiaramide, tinoridine, tolfenamic acid, zomepirac) neutralising antibodies (examples including etanercept and infliximab), antibiotics (examples including doxycycline and minocycline).

Any suitable route of administration can be used. For example, any of oral, topical, parenteral, ocular, rectal, vaginal, inhalation, buccal, sublingual and intranasal delivery routes may be suitable. The dose of the active agent will depend on the nature and degree of the condition, the age and condition of the patient and other factors known to those skilled in the art. A typical dose is from 0.1, e.g. 10 to 100, mg given one to three times per day.

The following Scheme and synthesis illustrate the preparation of compounds of formula I.

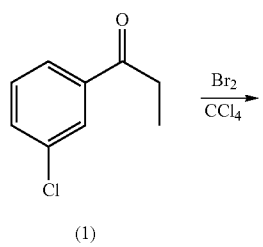

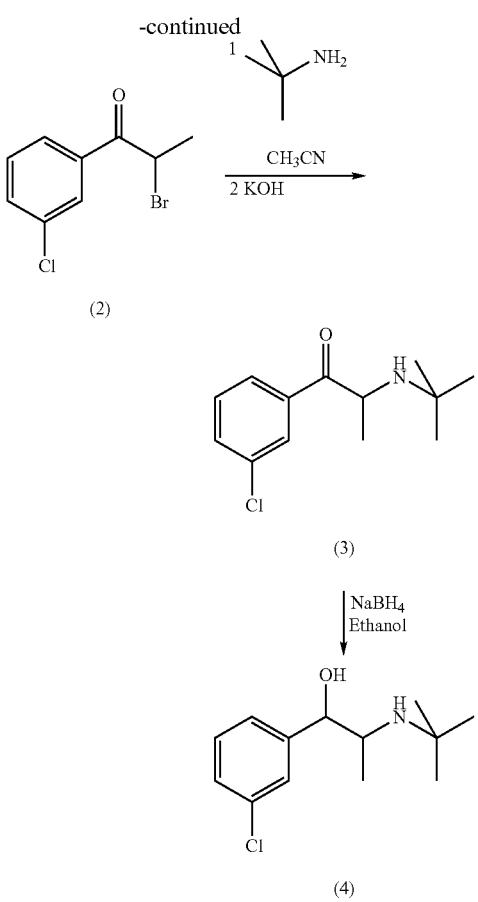

2-Bromo-1-(3-chlorophenyl)propan-1-one (2)

A 3-necked 2 L round bottomed flask equipped with a dropping funnel was charged with 3-chloropropiophenone (1) (110 g, 0.65 mol) and 770 ml of CH$_3$CN. The resulting reaction mixture was cooled to 0° C. under nitrogen. Bromine (33.4 ml, 0.65 mol) was added drop wise to the solution initially at 0° C. but during the addition (approximately ¼ of bromine was added) ice bath was removed [note: the reaction was scrubbed through 30% aqueous solution of sodium metabisulfite]. The reaction mixture was allowed to warm to 30° C. until initiation of the reaction occurred (gas evolution and decolourisation). The overall addition took 1.5 hours. After the addition was complete, the reaction mixture was then cooled to 0° C. and a saturated solution of sodium bicarbonate (~550 ml) was added carefully. The layers were separated and the aqueous layer was extracted with dichloromethane (3×440 ml). The combined organic layers were dried over anhydrous sodium sulphate, filtered and concentrated under vacuum to give a pale yellow solid (152 g, quantitative yield), which did not require any further purification and was used directly in the next step.

$^1$H-NMR (500 MHz, CDCl$_3$) $\delta_H$ 7.99 (s, 1H), 7.88 (d, 1H), 7.55 (d, 1H), 7.41 (m, 1H), 5.20 (m, 1H), 1.89 (d, 3H).

2-tert-Butylamino-1-(3-chlorophenyl)propan-1-one (3)

Crude 2-bromo-1-(3-chlorophenyl)propan-1-one (2) (152 g, 0.65 mol) was dissolved in 600 ml of acetonitrile (HPLC grade) in a 3-necked 2 L round bottomed flask fitted with a condenser and a dropping funnel. Tert-butylamine (172.5 ml, 1.63 mol) was added drop wise to the resulting mixture, at room temperature and under nitrogen. The reaction mixture was then heated to reflux for approximately 5 hours. During this time the reaction progress was monitored by TLC analysis (silica, hexane: ethyl acetate, 90:10). On consumption of the starting material, the reaction mixture was cooled to room temperature, filtered through celite and the celite washed with approximately 250 ml of ethyl acetate. The filtrate was washed with a 2M solution of KOH (350 ml). The layers were separated and the organic phase was dried over sodium sulphate anhydrous, filtered and concentrated to dryness to give a pale orange oil (147 g, quantitative yield), which did not need any further purification.

$^1$H-NMR (500 MHz, CDCl$_3$) $\delta_H$ 7.98 (s, 1H), 7.87 (d, 1H), 7.56 (d, 1H), 7.43 (m, 1H), 4.29 (m, 1H), 2.04 (broad singlet, 1H), 1.35 (d, 3H), 1.05 (s, 9H).

2-tert-Butylamino-1-(3-chlorophenyl)propan-1-ol (4)

147 g (0.65 mol) of the crude 2-bromo-1-(3-chlorophenyl)propan-1-one (3) was dissolved in 1500 ml of ethanol, in a 2 L round bottomed flask. The resulting solution was cooled to 0° C. under nitrogen and NaBH$_4$ (27.1 g, 0.72 mol) was added portion-wise while stirring. During the addition the temperature was kept below 5° C. After the final addition was complete, the reaction mixture was allowed to reach room temperature and was monitored by TLC analysis (silica, hexane: ethyl acetate, 50:50). On complete consumption of the starting material (approximately 1 hour), 147 ml of HCl (37%) were added until pH 1 was observed. Solid KOH (~25 g) in a minimal amount of water was then added until pH was adjusted at 7-8. The mixture was concentrated under reduced pressure. The resulting residue was basified further with solid KOH (~25 g) in a minimal amount of water, adjusting the pH to 10-11. The mixture was extracted into TBME (2×500 mL). The organic layers were combined, washed with brine, dried over anhydrous MgSO$_4$ and concentrated to yield a crude brown oil.

Purification: The crude material (127 g) was purified by gradient elution chromatography on silica gel (hexane: ethyl acetate, 90/10→hexane: ethyl acetate, 5:95). Single spot fractions were combined and reduced under reduced pressure to constant weight. This resulted in a low melting point solid as a mixture of distereoisomers (90.6 g, 58% yield).

$^1$H-NMR (500 MHz, CDCl$_3$) $\delta$ 7.16-7.37 (m, 10H, both diastereoisomers), 4.55 (d, 1H, major isomer), 3.84 (d, 1H, minor isomer), 3.08 (m, 1H, major isomer), 2.61 (m, 1H, minor isomer), 1.15 (s, 9H, major isomer), 1.14 (s, 9H, minor isomer), 1.01 (d, 3H, minor isomer), 077 (d, 3H, major isomer).

$^{13}$C-NMR (125 MHz, CDCl$_3$) $\delta_H$ 145.16, 144.19, 134.12, 134.00, 129.63, 129.42, 129.22, 127.65, 127.25, 126.97, 126.30, 125.57, 125.14, 124.35, 74.24, 71.95, 54.54, 51.84, 51.32, 51.29, 30.34, 30.18, 30.04, 20.39, 18.83, 17.81.

Mass Spec: 242 in +ve ESI

HPLC analysis: Erythro isomer 72.85%, Threo isomer 25.51%

The separate erythro isomers, and the threo diastereomeric pair of 2-tert-butylamino-1-(3-chlorophenyl)propan-1-ol were obtained by preparative Chiral HPLC, using a 330×50 CHIRALPAK® AD 20 µm column, a mobile phase of 90/10 CO2/ethanol+1% Diethylamine, a flow rate of 60 ml/min and a UV detection wavelength at 230 nm at a temperature of 25° C. 99 g of crude 2-tert-butylamino-1-(3-chlorophenyl)propan-1-ol were separated using this method to give:

(−)-(erythro)-2-tert-Butylamino-1-(3-chlorophenyl)propan-1-ol (5)

30.3 g of a light brown oil
Retention time 10.1 min
HPLC analysis (area % at 230 nm) >98
Isomeric purity >99

(+)-(erythro)-2-tert-Butylamino-1-(3-chlorophenyl)propan-1-ol (6)

29.6 g of a of a dark brown oil
Retention time 11.7 min
HPLC analysis (area % at 230 nm) >97
Isomeric purity >99

(+/−)-(threo)-2-tert-Butylamino-1-(3-chlorophenyl)propan-1-ol (7)

18.5 g of a pale brown oil
Retention time 12.4 and 14.6 min
HPLC analysis (area % at 230 nm) >98.5
Diastereomeric purity >99

(+/−)-(erythro)-2-tert-Butylamino-1-(3-chlorophenyl)propan-1-ol (8)

The following Assays provide evidence of the invention.
LPS Mouse Assay 7 week old Balb C ByJ mice (24-28 g) were administered, either by i.p. (5 ml/kg) or oral (10 ml/kg) administration, with vehicle or test article. 30 minutes later these animals were challenged with an intraperitoneal injection of 1 mg/kg LPS. 2 hours after LPS challenge blood samples were collected under light isoflurane anaesthesia into normal tubes by retro-orbital puncture. Samples were allowed to clot at room temperature and then spun at 6000 g for 3 min at 4° C. Serum was stored at −20° C. until use. Serum TNFα and IL-10 levels were analysed in duplicate by ELISA technique.

Bupropion (3) had a small effect on TNF alpha secretion induced by LPS at the top doses administered while its effect on IL-10 secretion was not present. The reduced forms of bupropion (7) (threo racemate) and (8) (erythro racemate) both had cytokine modulatory effects. (7) was the most potent agent, inhibiting TNF alpha at all doses administrated and potentiating IL-10 secretion at the higher doses. (7) was a considerably less potent cytokine modulator, having a small inhibitory effect on TNF alpha at the highest dose, and no real effect on IL-10 at any dose.

The erythro enantiomers (5) and (6) both had good cytokine modulatory profiles. (5) inhibited TNFα production after LPS stimulation, but had no effect on IL-10 levels. (6) however inhibited both TNFα and potentiated Il-10 secretion. Both molecules have a cytokine modulatory profile that highlights their potential as their anti-inflammatory and immunomodulatory treatments.

Carrageenan Paw Assay

Fasted (18 hour) male Wistar rats (105-130 g) were weighed and a basal mercury plethysmometer reading was taken of the right hind paw by submerging the paw in the mercury up to the tibiotarsal joint. Subsequently, vehicles, reference items and test articles were administered by oral gavage (10 ml/kg). Half an hour after treatment, 0.1 ml of 2% carrageenan in 0.9% saline was injected into the subplanatar area of the right hind paw. The right paw was measured again with the plethysmometer at 1, 2, 3, 4 and 5 hours after carrageenan administration. Paw volume effects was expressed as the area under the curve for paw volume over time. Activity (inhibition of paw volume) was expressed as the % antiinflammatory activity versus the vehicle control.

Compounds (5) and (6) each showed a dose-dependant anti-inflammatory effect against intraplantar carrageenan induced paw oedema.

Rat Adjuvant Assay

Male Wistar rats (180 to 200 g) were inoculated by subplantar injection of Freund's adjuvant (suspension of *Mycobacterium butyricum* in mineral oil) into the right paw at day 0. Sham inoculations were injected in the same way with 0.9% saline in matched Male Wistar rats. On day 2, animals were weighed. On days 3, 4, 7, 9 and 11, animals were weighed and both their right and left hind paws were measured by plethysymometry by submerging the paw up to the tibiotarsal joint. On day 11, rats with left hind paw volumes increased by 20% were selected for continuance in the study. On the same day, continuance rats were administered test article orally (10 ml/kg in distilled water) and from then on once a day until the completion of the study. Left and right hind paw volumes were measured on days 11, 14, 15, 16, 18 and 21.

Both compounds (5) and (6) had protective effects against adjuvant arthritis. (5) reduced paw oedema at the top two doses, while (6) inhibited paw inflammation at all doses (3, 10 and 30 mg/kg).

DSS Induced Colitis 8-10 week old BDF1 male mice (~30 g) were housed in normal conditions. At the start of the study normal water was exchanged for a 3% dextran sulphate solution to induce colonic inflammation. Concurrently actarit and the positive control budesonide were administered rectally twice a day for 7 days. On day 8 the animal were sacrificed and the large intestine was removed. The lower two thirds were assessed for histological severity (scoring system; 1 mild to 4 severe). Mice were assessed for cumulative rectal bleeding scores, diarrheal scores and cumulative hemoccult measurements.

Compounds (5) and (6) at the top dose both had a marked effect on histological scores induced by oral dextran sulphate. (6) was marginally more effective; a large ameliorating effect was seen at the lower dose. This suggests that both could have utility in treating inflammatory bowel disease.

Experimental Autoimmune Encephalitis

Acclimatised SJL mice were sensitised by a subcutaneous injection proteolipid protein (PLP) in Freund's complete adjuvant (CFA) acting as an encephalitogenic inoculum. Innoculum was administered subcutaneously at a concentration of 125 µg PLP/300 µg CFA in a volume of 200 µl. 48 hours later, an intraperitoneal injection of pertussis toxin (PTX) was administered at a dose of 20 µg/kg, to increase blood-brain barrier permeability.

Compound (6) was administered from the first day of the experiment and once a day until the end, orally at a dose of 10 mg/kg. Copaxone was administered intraperitoneally at a dose of 25 mg/kg. Throughout the experiment, careful clinical examinations and body weights were taken to observe the well being of the animal.

It was found that compound (6) completely ameliorated the second relapse of the SJL mouse EAE model.

The invention claimed is:

1. A method for the treatment an inflammatory bowel disease, wherein said method comprises administering, to a subject in need of such treatment, a compound of formula (I)

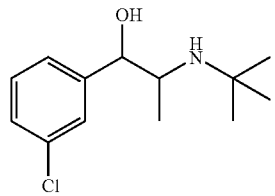

or a salt thereof wherein the compound is an individual erythro enantiomer, a racemic or non-racemic mixture of the erythro pair of diastereoisomers.

2. The method according to claim 1, where the compound is a racemic or non-racemic mixture of the erythro pair of diastereoisomers.

3. The method according to claim 1, wherein the compound is (1S,2R)-erythro-2-(1,1-dimethylethyl)amino-1-(3-chlorophenyl)propan-1-ol or (1R,2S)-erythro-2-(1,1-dimethylethyl)amino-1-(3-chlorophenyl)propan-1-ol.

4. The method according to claim 1, wherein the subject of treatment is further administered with another therapeutic agent selected from corticosteroids, cytotoxics, antibiotics, immunosupressants and non-steroidal anti-inflammatory drugs.

5. The method according to claim 4, wherein the compound (I) and said another agent are provided in combination.

* * * * *